(12) United States Patent
Offenbacher (10) Patent No.: US 8,840,765 B2
(45) Date of Patent: Sep. 23, 2014

(54) OXYGEN SENSOR WITH A MICROPOROUS ELECTROLYTE LAYER AND PARTIALLY OPEN COVER MEMBRANE

(75) Inventor: Helmut Offenbacher, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/293,275

(22) Filed: Nov. 10, 2011

(65) Prior Publication Data

US 2012/0168322 A1 Jul. 5, 2012

(30) Foreign Application Priority Data

Nov. 10, 2010 (EP) ..................................... 10190756

(51) Int. Cl.
*G01N 27/26* (2006.01)
*G01N 33/49* (2006.01)
*G01N 27/404* (2006.01)
*G01N 27/28* (2006.01)

(52) U.S. Cl.
CPC .............. *G01N 27/404* (2013.01); *G01N 27/28* (2013.01); *G01N 33/4925* (2013.01)
USPC ........... 204/431; 205/775; 205/783; 205/792; 204/400

(58) Field of Classification Search
USPC ........... 205/778.5, 775, 779, 782, 783, 785.5; 204/430, 431, 432, 400
See application file for complete search history.

(56) References Cited

U.S. PATENT DOCUMENTS

| 4,859,306 | A | * | 8/1989 | Siddiqi et al. | ................ 204/416 |
|---|---|---|---|---|---|
| 4,933,048 | A | | 6/1990 | Lauks | |
| 5,387,329 | A | | 2/1995 | Foos et al. | |
| 7,232,511 | B1 | | 6/2007 | Venkatasetty | |
| 7,586,242 | B2 | | 9/2009 | Yokoyama et al. | |
| 2004/0033414 | A1 | | 2/2004 | Rohrl | |
| 2006/0007171 | A1 | | 1/2006 | Burdi et al. | |
| 2006/0021873 | A1 | | 2/2006 | Mett | |
| 2006/0293169 | A1 | | 12/2006 | Srinivasan et al. | |
| 2008/0209876 | A1 | | 9/2008 | Miller | |
| 2010/0252428 | A1 | | 10/2010 | Lauks et al. | |

FOREIGN PATENT DOCUMENTS

| EP | 0097554 A2 | 1/1984 |
|---|---|---|
| EP | 0299780 A2 | 1/1989 |
| EP | 0805973 B1 | 11/1997 |
| GB | 2308193 A | 6/1997 |
| JP | 9-127045 A | 5/1997 |
| WO | 0136957 A1 | 5/2001 |
| WO | 2009090094 A1 | 7/2009 |

OTHER PUBLICATIONS

European Search Report issued Feb. 27, 2012 in Application No. EP 11188648.7, 6 pages.

* cited by examiner

*Primary Examiner* — Alex Noguerola
*Assistant Examiner* — Maris R Kessel
(74) *Attorney, Agent, or Firm* — Roche Diagnostics Operations, Inc.

(57) ABSTRACT

The present invention concerns an electrochemical sensor for determining oxygen dissolved in an aqueous measuring medium, a process for its production as well as a method for determining oxygen dissolved in an aqueous measuring medium using the electrochemical sensor.

11 Claims, 7 Drawing Sheets

OXYGEN SENSOR WITH A MICROPOROUS ELECTROLYTE LAYER AND PARTIALLY OPEN COVER MEMBRANE

TECHNICAL FIELD

The disclosed embodiments relate to electrochemical sensors for determining oxygen dissolved in an aqueous measuring medium and, more particularly, an oxygen sensor with a microporous electrolyte layer and partially open cover membrane, a process for its production as well as a method for determining oxygen dissolved in an aqueous measuring medium using the electrochemical sensor.

BACKGROUND

Sensors for analysing body fluids are often principal components of clinically relevant analytical methods. In this connection a rapid and precise measurement of analytes is of primary interest that allows the determination of so-called point-of-care parameters. Point-of-care examinations are often carried out above all in intensive care units and in anaesthesia departments, but also in outpatient departments. These so-called emergency parameters include among others the blood gas values (and here in particular the oxygen content and carbon dioxide content), the pH value, electrolyte values as well as certain metabolite values.

Point-of-care examinations have the advantage that the results are already available after a short time because, on the one hand, the samples do not have to be transported to a specialized laboratory and, on the other hand, one does not have to allow for the time schedules of the laboratory. In order to enable emergency parameters to be determined as near as possible in time, sensors are used that are designed for a multiple analyte determination, which sensors should in principle have a high in-use lifetime in order to increase the period between regular sensor replacements, which are for example required after a predetermined maximum period of use has expired or after a predetermined number of measurements have been carried out. This reduces the time needed for the sensor replacement during which such a point-of-care analyzer is not able to be used, i.e., is not available for measurements. Furthermore, the sensor activation time that directly follows a sensor replacement, which specifies the time period from the sensor replacement until a new sensor is able to be used for analytical measurements, should be kept as short as possible.

Test strips and also medical analyzers with multi-use sensors can for example be used to carry out such point-of-care examinations, which reduces the manual labor for carrying out the examinations to a minimum. Sensors for a point-of-care use are usually operated in an almost completely automated manner in appropriately equipped analytical measuring devices and often require only a few and simple interventions by the user from the sample preparation up to the provision of the test result. They can be designed for a single as well as for a repeated measurement of the parameters to be determined.

The measurement of oxygen or its partial pressure ($pO_2$) in an aqueous measuring medium can for example be carried out using amperometric sensors comprising at least one working electrode and at least one counter electrode. In the case of electrodes of the Clark type, a gas-permeable and a substantially ion-impermeable and liquid-impermeable membrane spatially separates the sample space from the inner electrolyte space. The inner electrolyte space is filled with an electrolyte solution in which a working electrode and a counter electrode are located. An electrode arrangement with a microporous inner electrolyte layer is described in, for example, WO 2009/090094 A1.

An important criterion in the development and provision of electrochemical sensors for point-of-care examinations are the special requirements regarding the measuring conditions and in particular regarding the usually only small volume of sample that is available. Thus, generally only small amounts of sample (e.g., 100 µl or less) are available for the determination of emergency parameters. If it is intended to determine a large number of parameters using small amounts of sample, the individual electrodes and the distances between them should be as small as possible.

Another important criterion in the development and provision of electrochemical sensors for point-of-care examinations is, as mentioned above, their lifetime. In this connection there is the need to achieve a long-lasting shelf life before the sensor is put into operation as well as a high in-use lifetime of the electrochemical sensor.

In order to ensure a long-lasting shelf life, the electrodes located in the electrochemical sensor should be stored dry, i.e., essentially free of water, and only be brought into contact with the liquid inner electrolyte directly before they are put into operation. For this purpose the liquid inner electrolyte can for example be formed in situ by contacting the dry sensor with an aqueous solution before start-up whereby water diffuses into the inner electrolyte space and dissolved ions located there with formation of the liquid inner electrolyte.

In order to achieve a high in-use lifetime of for example at least 500 measurements or 3 to 4 weeks, as is desired for modern point-of-care analyzers, the various layers of the electrochemical sensor must also be compatible with one another. Thus, in particular they should not become detached from one another or form cracks such as can for example be caused by swelling.

Finally, as explained above, the ability to rapidly activate an electrochemical sensor that is being used for the first time for analytical measurements in an analyzer plays an important role. Hence, in order to enable analytes in a sample to be rapidly determined, the time period between inserting a new electrochemical sensor into an analyzer and its being available for use for analytical measurements should be as short as possible.

EP 0 805 973 B1 discloses a device as well as a method for measuring the concentration of gases in a sample. An electrochemical sensor serves as the device which comprises a working electrode, a counter electrode, an electrolyte layer and a gas-permeable membrane where the electrolyte layer consists of a photo-formed proteinaceous gel. In order to prevent a premature contamination of the negatively polarized working electrode (cathode) consisting of gold by positively charged silver ions originating from the counter electrode (anode) consisting of silver, the spacing between the two electrodes that are in electrical contact via a gel layer must be at least 1 mm.

U.S. Pat. No. 5,387,329 describes a planar electrochemical oxygen sensor in which a swellable polymer whose swelling rate is less than twice its dry volume is used as a hygroscopic electrolyte, and in this process forms a hydrophilic electrolyte layer that is permeable to water and cations. A swellable polymer that is preferred in the context of this document is Nafion®, a sulfonated tetrafluoroethylene polymer whose lithium charged sulfonate groups give the polymer ionomeric properties and result in an exchange of lithium ions for silver ions. This has the effect that in the case of an amperometric oxygen sensor with a silver counter electrode, the effective migration rate of the silver ions to the working electrode is lowered.

The electrolyte layers used in EP 0 805 973 B1 and U.S. Pat. No. 5,387,329 have disadvantages. Thus, for example, the production of very thin layers (about 1 μm) of swellable polymers (such as, e.g., the photo-formed proteinaceous gels in EP 0 805 973 B1) is very laborious.

Furthermore, the silver ions released during the operation of an oxygen sensor rapidly lead to interfering signals as well as an increase of the measurement signal and of the zero point in the case of very thin layers and very small electrolyte volumes, where the zero point specifies the current which flows across the oxygen sensor at 0% oxygen in the sample. On the other hand, the use of thicker, swelling layers (about 10-50 μm) in a multilayer construction promotes the formation of leaks in the layer structure. This makes it difficult to achieve the desired long-life of the sensor.

An important disadvantage of thin, water-containing polymer layers is also that, after applying an electrical field, interfering silver ions migrate between the two electrodes on a direct path through the polymer and thus reach the working electrode and contaminate it after a relatively short operating period which considerably limits the effective period of use of such preferably planar oxygen sensors.

WO 2009/090094 A1 discloses an electrochemical sensor in which the disadvantages described above are at least partially eliminated. For this purpose the electrochemical sensor contains an electrolyte layer located between the working electrode and the counter electrode, the electrolyte layer comprising at least one particulate material and at least one binding agent. In this case the particulate material which is preferably an alumosilicate such as, for example, a zeolite and the binding agent forms a microporous layer which then can be permeated by a liquid electrolyte.

In contrast to a gel-like electrolyte layer as described for example in EP 0 805 973 B1, silver ions generated at the counter electrode of such an electrochemical sensor have to migrate through a labyrinth of micropores on their way to the working electrode which slows down the migration rate of the silver ions. Furthermore, in a preferred variant WO 2009/090094 A1 provides the possibility that the particulate material additionally has ion-exchange groups to which the silver ions can at least temporarily bind. These two measures can increase the lifetime of the electrochemical sensor to about three to four weeks.

SUMMARY

It is against the above background that the embodiments of the present invention provide certain unobvious advantages and advancements over the prior art. In particular, the inventor has recognized a need for improvements in electrochemical sensors for the determination of oxygen dissolved in an aqueous measuring medium.

Although the present invention is not limited to specific advantages or functionality, it is noted that the present invention provides an electrochemical sensor for determining oxygen (also referred to in the following as (gaseous) analyte) in which further disadvantages of the prior art are at least partially eliminated. In particular, the sensor should ensure a short activation time when used for the first time in addition to a long-lasting shelf life and a high in-use lifetime. In addition it should be possible to manufacture the sensor in a simple and cost-effective manner.

In accordance with one embodiment of the present invention, an electrochemical sensor for the determination of oxygen dissolved in an aqueous measuring medium is provided that comprises a working electrode and a counter electrode, an electrolyte layer arranged between the working electrode and the counter electrode, and a gas-permeable cover layer arranged over the electrolyte layer. The electrolyte layer comprises at least one particulate material and at least one binding agent which together form a porous, non-swellable framework structure. The pores of the non-swellable framework structure are intended to take up a liquid electrolyte or they contain this liquid electrolyte. The gas-permeable cover layer comprises at least one opening which enables a contact of a partial area of the electrolyte layer with the aqueous measuring medium.

In accordance with another embodiment, a process for producing an electrochemical sensor is provided comprising: (a) providing at least one particulate material, (b) mixing the particulate material with at least one binding agent and optionally further substances, (c) processing the mixture obtained in step (b) to form a paste, (d) applying the paste obtained in step (c) to a carrier comprising a working electrode and a counter electrode and hardening the paste applied to the carrier, and (e) applying a gas-permeable cover layer comprising at least one opening to the carrier obtained in step (d). The process can also further comprise introducing a layer of a hydrophilic polymeric filling material into the opening of the gas-permeable cover layer applied to the carrier in step (e).

In accordance with yet another embodiment, a method for the determination of oxygen dissolved in an aqueous measuring medium is provided comprising bringing the aqueous measuring medium into contact with an electrochemical sensor, and determining the oxygen dissolved in the aqueous measuring medium by measuring a signal generated by the electrochemical sensor.

These and other features and advantages of the present invention will be more fully understood from the following detailed description of the invention taken together with the accompanying claims. It is noted that the scope of the claims is defined by the recitations therein and not by the specific discussion of features and advantages set forth by the present description.

BRIEF DESCRIPTION OF THE DRAWINGS

The following detailed description of the embodiments of the present invention can be best understood when read in conjunction with the following drawings, where like structure is indicated with like reference numberals and in which.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiment(s) of the present invention.

DETAILED DESCRIPTION

The working electrode and the counter electrode of the electrochemical sensor according to the invention can consist of any material which appears suitable to a person skilled in the art for the purposes of the present invention. The working electrode can for example be formed from gold or from a composite material based on gold. But other metals are also conceivable such as, for example, silver. In contrast, the counter electrode is typically formed from silver or from a composite material based on silver.

The electrochemical sensors of the present invention additionally comprise an electrolyte layer which is arranged between the working electrode and the counter electrode. This electrolyte layer is formed from at least one particulate material and at least one binding agent which together form a porous, non-swellable framework structure the pores of which are situated between the individual particles of the particulate material. Compared to a pure polymer layer or gel layer, the pore labyrinth formed in this manner increases the distance which has to be travelled by the ions moving between the electrodes and thus increases the lifetime of the sensor.

Particulate materials which can be used in the electrochemical sensor of the present invention can be of an inorganic or organic type and in particular comprise dense inorganic materials or dense (unplasticized) organic polymers. Typical inorganic particulate materials comprise controlled porous glass (CPG), silica gels, silicates and alumosilicates (also referred to as aluminosilicates) which are primarily selected from the group consisting of framework silicates and layer silicates. Organic polymers which can be used according to the invention as a particulate material can comprise for example microparticles made of polystyrene, polyamide, polyvinyl chloride, polyvinylidene chloride, poly(meth)acrylate, polyacrylonitrile as well as copolymers thereof, but are not limited to these.

The use of a naturally occurring or synthetic alumosilicate has proven to be advantageous within the scope of the invention and, more typically, the use of a synthetic alumosilicate. The term "synthetic alumosilicate" as used within the scope of the present invention encompasses fully synthetic alumosilicates as well as alumosilicates which are obtained by artificially modifying (e.g., chemically modifying) a naturally occurring alumosilicate. Examples of naturally occurring or synthetic alumosilicates comprise feldspars, mica, mullite, sillimanite and zeolites, but are not limited to these.

In a typical variant of the electrochemical sensor according to the invention, the particulate material can have channels and in particular channels having a diameter between about 0.1 nm and about 10 nm, and optionally ion exchange groups. In another typical embodiment the particulate material is a zeolite such as, for example, faujasite, chabazite, mordenite or natrolite in which polyhedrons, layers or chains of corner-linked $[(Al, Si)O_4]$ tetrahedrons are present which form an anionic spatial network that is permeated by channels.

Depending on the type of the zeolite the channels have a diameter of about 0.5 nm to about 5.0 nm, typically of about 0.7 nm to about 2.0 nm, and contain ion exchange groups and, in particular, cation exchange groups on their inner and outer surfaces. The use of zeolites having an inner channel structure and ion exchange groups has proven to be particularly advantageous especially for amperometric electrodes of the Clark type. The sensor according to embodiments of the invention typically comprises faujasite, more typically faujasite-Na as the particulate material.

Due to their channel-containing structure, zeolites have a large inner surface which can come into contact with a liquid electrolyte. Because ions of a suitable size which are present in the electrolyte liquid can migrate through the channels of the zeolite, it is possible to reduce the amount of undesired ions. Thus, especially with electrochemical sensors which comprise silver-containing counter electrodes the problem occurs that when the sensor is put into operation silver ions are released from the counter electrode, migrate towards the working electrode and are deposited on this electrode as elemental silver thus passivating the working electrode.

Similar processes also occur with other metals used as electrode materials such as, for example, lead which can release lead ions upon contact with the electrolyte liquid that can also act as interfering cations. By using an electrochemical sensor according to the present invention it is possible to increase the effective distance travelled between the counter electrode and working electrode and thus reduce the risk of a rapid passivation of the working electrode which manifests itself in a longer lifetime of the sensor.

On the other hand, certain particulate materials such as, for example, zeolites can also act as ion exchangers due to their anionic framework structure. Thus, for example silver ions released at the counter electrode and which migrate towards the working electrode can be absorbed by zeolites and exchanged for suitable less critical cations such as sodium ions which reduces the amount of free silver ions in the electrolyte and can counteract a passivation of the working electrode which also leads to a longer lifetime of the electrochemical sensor.

The size of the particles of the particulate materials can be varied according to the respective requirements. Within the scope of the present invention the particles of the particulate material usually have an average particle diameter of about 0.1 µm to about 10 µm, where an average particle diameter of about 1.0 µm to about 5.0 µm is typical. In any case the particle size of the porous material should always be smaller than the layer thickness of the electrolyte layer which is in the range of about 5 µm to about 30 µm, typically in the range of about 10 µm to about 20 µm.

In addition to the particulate material the electrolyte layer comprises at least one binding agent as a further component. The binding agent is typically an organic binding agent such as, for example, a crosslinked or uncrosslinked, linear or branched organic polymer. More typically, the organic binding agent contained in the electrolyte layer is any crosslinked or uncrosslinked synthetic polymer which is typically selected from the group comprising a phenol resin, an epoxide resin, a vinyl resin, a PVC copolymer, a two-component epoxide resin, a polyurethane resin system and a UV-curable polyacrylate monomer mixture. A phenol resin and in particular a crosslinked phenol resin is more typically used as the cross-linked or uncrosslinked synthetic polymer.

The typically non-swellable binding agent is used in such quantities that it binds the particles of the inorganic or organic particulate material to form a porous, non-swellable framework structure. This means that the binding material does not completely fill out the interspaces between the particles of the particulate material so that a non-swellable framework structure is formed which has pores having a diameter of about 500 nm to about 5 μm, typically of about 1 μm to about 3 μm. According to embodiments of the invention, the porous, non-swellable framework structure results in a relative uptake of liquid of about 20% by weight to about 50% by weight, typically of about 26% by weight to about 44% by weight based on the dry weight of the porous, non-swellable framework structure.

Figure 2A:
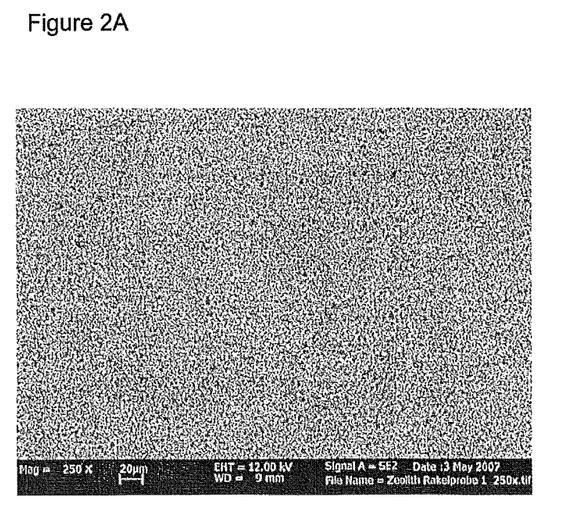
FIGS. 2A and 2B each show electron micrographs of the porous electrolyte layer in an electrochemical sensor according to one or more embodiments of the present invention.
Figure 2B:
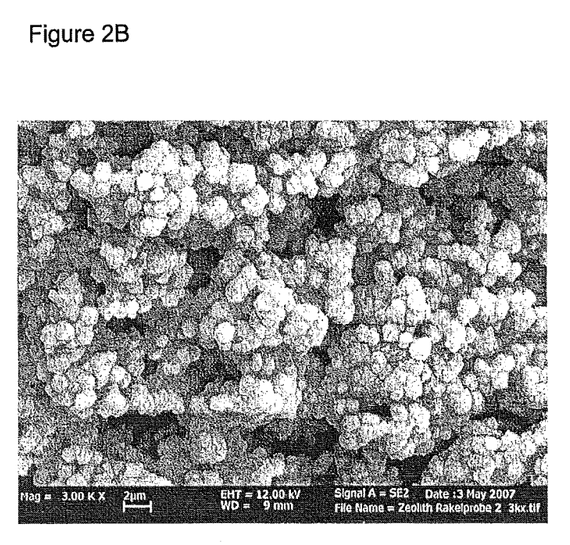

The required amounts of binding agent can vary depending on the type and amount of the particulate material that is used as well as on the desired pore size and can be adapted to the respective requirements by a person skilled in the art. FIGS. 2A and 2B each show electron micrographs of the electrolyte layer of such a sensor in which particles of a particulate material are bonded to form a porous, non-swellable framework structure using a binding agent. The porous, non-swellable framework structure has a regular distribution of pores and consists of units which as a rule are about 1 to 3 particles wide and are linked in a chain-like manner.

According to an embodiment of the invention, the electrolyte layer can, in addition to the at least one particulate material and the at least one binding agent, also comprise one or more auxiliary substances. Auxiliary substances which can be used for this purpose comprise in particular synthetic cellulose derivatives such as, for example, alkyl celluloses where the teuu "alkyl" represents a straight-chained or branched hydrocarbon residue containing 1 to 6 carbon atoms. Typical alkyl celluloses in the sense of the present invention are selected from the group comprising methyl cellulose, ethyl cellulose, propyl cellulose, ethylmethyl cellulose and propylmethyl cellulose. The wettability of the surface of the structure with the liquid electrolyte can be improved by adding small amounts of these alkyl celluloses. Further suitable auxiliary substances comprise for example antifoaming agents.

The liquid electrolyte which ensures a conducting electrolyte connection between the working electrode and the counter electrode in the electrochemical sensor, according to an embodiment of the present invention, can be any electrolyte, e.g., an electrolyte based on water which, when a voltage is applied, results in a transport of charge carriers due to the directed movement of ions. Within the scope of the present invention it is typical that the liquid electrolyte contains an alkali metal chloride.

In particular, sodium and/or potassium chloride can be used as an alkali metal chloride which serves as a conducting salt component of the liquid electrolyte in an electrochemical sensor according to the present invention. The use of sodium and/or potassium chloride as the main component of the electrolyte has the advantage that the silver ions released from the counter electrode when using silver-containing counter electrodes are additionally hindered in their migration towards the working electrode due to silver chloride precipitation as a result of which the deposition of elemental silver on the working electrode can be reduced.

In a typical embodiment the liquid electrolyte additionally contains at least one water-soluble polymer in addition to the alkali metal chloride. Any polymer can be used as a water-soluble polymer which increases the viscosity of the liquid when introduced into the liquid electrolyte solution described above and thus also can contribute to a reduction of the migration rate of released ions, for example released silver ions. Water-soluble polymers which can be used within the scope of the present invention are for example polyethylene glycol, polyvinyl pyrrolidone (PVP) and alkylpolyglycosides, where the electrolyte liquid typically contains polyethylene glycol and/or polyvinyl pyrrolidone as the water-soluble polymer.

Within the scope of one or more embodiments of the present invention, the electrolyte layer comprises the non-volatile components of the liquid electrolyte before the electrochemical sensor is put into operation. For this purpose a liquid containing these components and typically the liquid electrolyte can be introduced into the pores of the non-swellable framework structure, for example, by being added dropwise and after removing a supernatant of electrolyte liquid, for example, by blotting, stored for a period of several hours, e.g., for a period of 48 hours or more at a temperature of >25° C., e.g., at a temperature of 65° C., in order to enable the volatile components of the liquid electrolyte to evaporate. This can ensure that after the drying step, the non-volatile components of the electrolyte such as, for example, alkali metal chlorides as well as other substances, which include among others water-soluble polymers, are present in the electrolyte layer of the electrochemical sensor.

Alternatively the non-volatile electrolyte components can already be added to a mixture containing the at least one particulate material, the at least one binding agent and optionally further substances which is present for example in the form of a paste before forming the porous, non-swellable framework structure. The mixture obtained in this manner can be subsequently hardened to form a porous, non-swellable framework structure the pores of which contain the non-volatile components of the liquid electrolyte. This procedure has the advantage over the method described above, i.e., compared to introducing the liquid electrolyte into the pores of an already existing framework structure, the advantage being that the various components of the liquid electrolyte can be introduced into the porous, non-swellable framework structure of the sensor according to the invention in a simpler, more homogeneous and more reproducible manner.

The electrochemical sensors of the present invention furthermore comprise one gas-permeable cover layer arranged over the electrolyte layer described above, said cover layer comprising at least one opening and which thus enables contact of a partial area of the electrolyte layer with the aqueous measuring medium. The term "contact of a partial area of the electrolyte layer with the aqueous measuring medium" is to be understood functionally within the scope of the present application. It is important that no material of the cover layer itself is present in the area of the opening of the cover layer, i.e., the continuous cover layer described in the prior art is interrupted in this area and thus the properties of the cover layer and in particular its gas-permeability as well as its substantial ion impermeability and liquid impermeability are functionally not effective in this area.

Within the scope of the present application the term "contact of a partial area of the electrolyte layer with the aqueous measuring medium" is thus not only to be understood as a direct contact as for example is caused by a slit-shaped or hole-shaped opening in the gas-permeable cover layer but also an indirect contact such as one effected by a slit-shaped or hole-shaped opening in the cover layer that is filled with a suitable material. In this connection it is only important that the material used to fill the opening is not identical to the material of the gas-permeable cover layer in order to not again obtain a completely closed gas-permeable cover layer with the said disadvantages.

Due to the at least one opening in the gas-permeable cover layer the activation time of the electrochemical sensors can be considerably reduced when used for the first time, which in the relevant art is also described as "wet-up" time, compared to electrochemical sensors with a completely closed gas-permeable cover layer as a result of which the electrochemical sensors according to the invention are more rapidly ready to use for analytical measurements. For this purpose reference liquids such as, for example, calibration solutions or conditioning liquids are usually used, which are regarded to be functionally equivalent to the measuring media within the scope of the present application.

In order to evaluate the activation time of an electrochemical sensor, it is possible for example to record the change of the standby current measured for the sensor over time. In this connection standby current refers to that current which for example in the case of an oxygen sensor flows across the cathode under standby conditions when a voltage of 700 mV is applied, where standby conditions are understood to mean the contact of the oxygen sensor with a calibration solution which has an oxygen content that matches the oxygen partial pressure in the air.

The standby current is determined at an oxygen partial pressure $pO_2$=147 mmHg (corresponds to the $pO_2$ value corresponding to that of the ambient air of a calibration solution at a barometric pressure of about 750 mmHg at 37° C.) and is composed of two components:
(i) a constant component independent of the $pO_2$ value of the calibration solution, and
(ii) a variable component dependent on the $pO_2$ value of the calibration solution.

In the case of an idealized sensor the constant current component is zero, i.e., the measured current is also zero at an oxygen partial pressure of 0 mmHg. The constant $pO_2$ value independent signal component is referred to as the zero point current. In the case of real sensors the zero point current is, however, usually >0. The variable $pO_2$ value dependent signal component is referred to as the slope and is the change in current (in [nA]) when the oxygen partial pressure changes from 0 to 147 mmHg.

If the zero point current is >0 and one calculates which oxygen value corresponds to this current in the case of an ideal sensor (i.e., if no constant signal component would be present) one obtains by definition the gas zero point in mmHg. Thus, the gas zero point corresponds to the constant signal component of a real sensor expressed as the $pO_2$ value (in [mmHg]) where, as a model, it is assumed for the calculation that the signal component of the sensor at 0 mmHg is actually zero.

A group of electrochemical sensors with a completely closed gas-permeable cover layer exhibits a considerable decrease and a large drift of the gas zero point (see FIG. 3A) and of the slope (see FIG. 4A) until the regulated range is reached especially within the first hours after the first contact with a calibration solution. In particular the measurement signals of a group of such electrochemical sensors exhibit large fluctuations and sometimes significant jumps in these parameters in this period after first activation of the sensor as a result of which the measurement signal sometimes fluctuates so strongly that a reliable analyte determination is often not possible in this phase even taking into account possible corrections of the sensor signal drift.

In contrast, the gas zero point (see FIG. 3B) and the slope (see FIG. 4B) of a group of electrochemical sensors according to an embodiment of the present invention with an at least partially open cover membrane are already in the regulated range at the start of the measurement and exhibit a drift which is within the specifications without the strong fluctuations in these parameters which sometimes occur in the prior art as a result of which reliable analyte determinations are already possible at an earlier time also with the aid of additional possible corrections of the sensor signal drift.

Figure 3A:
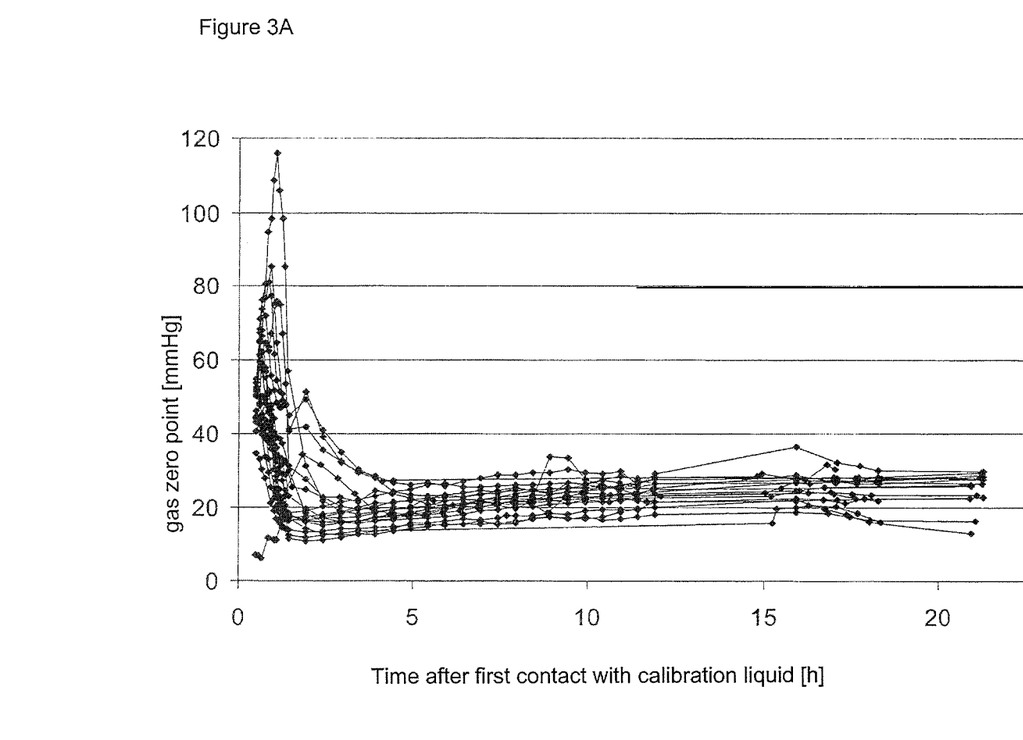
FIG. 3A shows the gas zero point [mmHg] of a group of electrochemical $pO_2$ sensors with a closed cover membrane according to the prior art with respect to time after first contact with the calibration liquid [h]
Figure 3B:
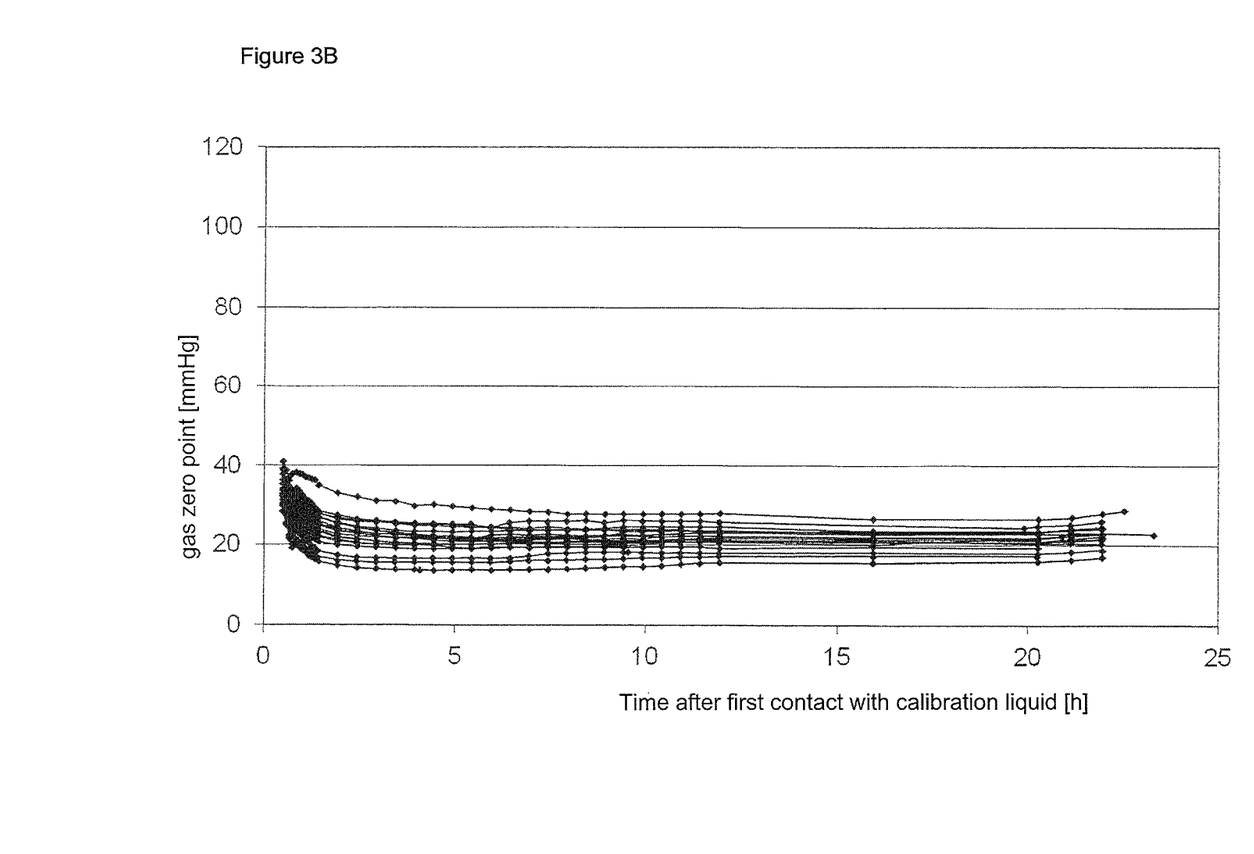
FIG. 3B shows the gas zero point [mmHg] of a group of electrochemical $pO_2$ sensors with a partially open cover membrane according to an embodiment of the present invention with respect to time after first contact with the calibration liquid [h]
Figure 4A:
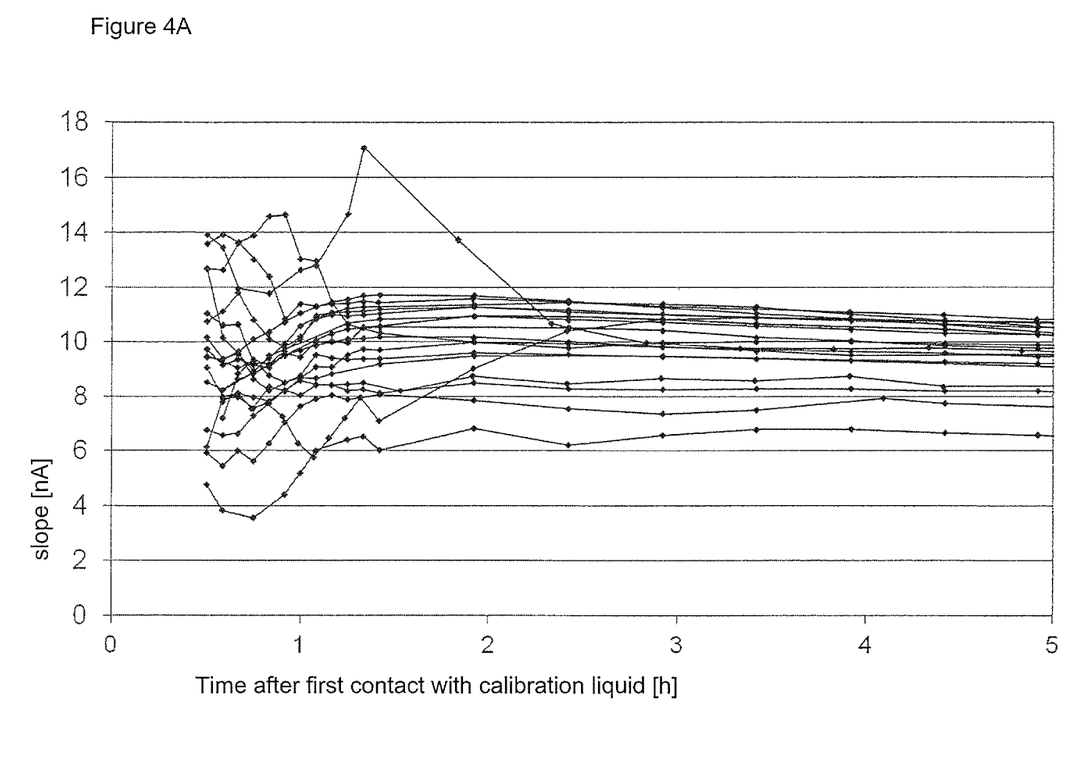
FIG. 4A shows the slope [nA] of a group of electrochemical $pO_2$ sensors with a closed cover membrane according to the prior art with respect to time after first contact with the calibration liquid [h]
Figure 4B:
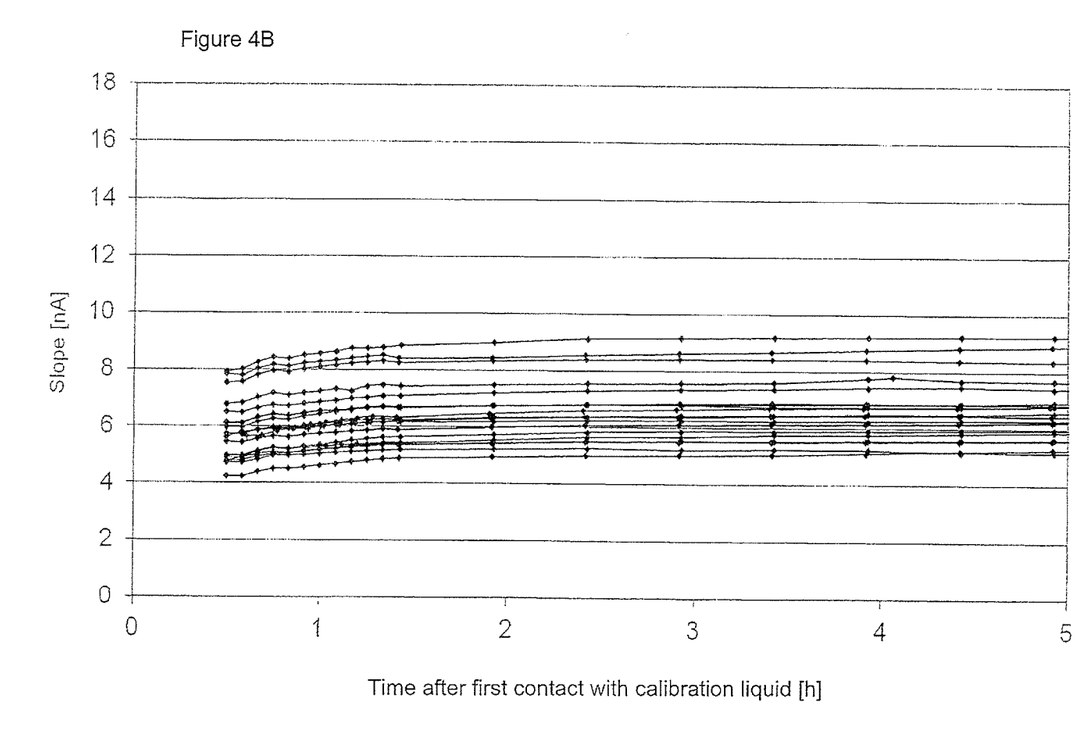
FIG. 4B shows the slope [nA] of a group of electrochemical $pO_2$ sensors with a partially open cover membrane according to an embodiment of the present invention with respect to time after first contact with the calibration liquid [h].

In FIGS. 3 and 4 the time (in [h]) after the sensor (which is previously stored dry) is brought into contact for the first time (t=0) with the appropriate reference liquids such as, for example, calibration liquids or conditioning liquids, is plotted on the x axis. In principle the sensor can be activated in an analogous manner but also using other liquids such as, for example, measuring media.

The reason for the phenomenon that electrochemical sensors with a completely closed gas-permeable cover layer yield high standby currents at the beginning of the sensor activation phase may be the displacement of air that is present in a dry state and its compression due to hydration of the inner electrolyte space. Thus, the residual air in the inner electrolyte space may result in a shorter diffusion path of the gaseous analyte from the sample to the working electrode which can lead to higher currents. Successive breakdown of the residual air contained in the inner electrolyte space during the wet-up phase results in a normalization of the behaviour of the electrochemical sensor until finally a gas-bubble-free inner electrolyte space required under stable operating conditions is present.

In contrast, the diffusion behaviour of oxygen in the electrochemical sensors of the present invention remains much more defined due to the opening within the gas-permeable cover layer. Air voids in the inner electrolyte space that can occur at the beginning of the sensor activation can be degraded more effectively by means of the cross diffusion in the microporous electrolyte layer, especially in the case of a hypobaric sensor activation.

Furthermore, the at least one opening contained in the gas-permeable cover layer has the effect that for example silver ions formed at the counter electrode can diffuse away into the sample space above the electrochemical sensor which reduces the concentration of free silver ions in the electrolyte layer and thus reduces the formation of silver nuclei and the precipitation of colloidal silver within the porous, non-swellable framework structure. This allows the in-use lifetime of the electrochemical sensor to be increased to considerably more than four weeks and thus further improved compared to the sensors known from the prior art.

The at least one opening in the gas-permeable cover layer can in principle be of any size and/or shape that appears suitable to a person skilled in the art to achieve a shorter sensor activation time. If the gas-permeable cover layer has several openings then they are typically arranged outside the area of the electrodes and the openings can be of the same size and/or shape, or of different sizes and/or shapes. In a typical variant of the invention the at least one opening has a width in the range of about 50 μm to about 500 μm, more typically in the range of about 100 μm to about 300 μm.

With regard to the geometric shape the at least one opening typically has a slit-shaped or is window-like, where a slit-shaped opening in the sense of the present application is understood to mean that the gas-permeable cover layer in this case is present in the form of two not directly linked partial areas that are typically arranged parallel to one another. In contrast, a window-like opening refers to any round, oval or angular opening which does not result in any division of the gas-permeable cover layer into at least two partial areas that are not directly joined to one another.

With regard to the spatial arrangement of the at least one opening, the electrochemical sensors according to the invention envisage that basically the opening can be formed at any position on the gas-permeable cover layer. The at least one opening is, however, at least partially, i.e., partially or completely, arranged above the area of the electrolyte layer that lies between the working electrode and the counter electrode. Such an arrangement has the advantage that mainly silver ions which are located in the area of the electrolyte layer lying between the working electrode and the counter electrode are transported away into the sample space above the sensor thus allowing a reduction in particular of the precipitation of colloidal silver within the porous, non-swellable framework structure formed between the two electrodes.

In the electrochemical sensors of the present invention the at least one opening contained in the gas-permeable cover layer is unfilled in one embodiment. In an alternative embodiment it is possible that the opening is filled with a suitable hydrophilic polymeric filling material where the hydrophilic polymeric filling material differs from the material from which the gas-permeable cover layer is formed. Hydrophilic polymeric filling materials which can be used within the scope of the present application comprise for example hydrogels, where hydrogels made of polyether-polyurethane copolymers or polyvinyl pyrrolidone (PVP) are especially typical.

The hydrophilic polymeric filling materials typically have a high permeability for water-soluble substances of low-molecular weight, in particular for ionic substances and for water molecules. This enables on the one hand, a (compared to completely closed cover layers) more rapid entry of water into the electrochemical sensor during the wet-up phase. On the other hand, in contrast to completely closed cover layers this allows silver ions to diffuse out of the electrochemical sensor into the sample space while at the same time for example blood components of high molecular weight and cells from the sample are prevented from diffusing into the electrolyte layer.

The gas-permeable cover layer formed according to the invention allows gaseous analytes to penetrate into the electrochemical sensor (under normal conditions) but substantially prevents the entry of in particular ions and/or nonvolatile components of the aqueous measuring medium into the electrochemical sensor at all sites with the exception of the opening that is present according to the invention.

In a typical embodiment the gas-permeable cover layer is designed such that it completely covers the working electrode and at least partially, i.e., partially or completely covers the counter electrode. The term "covers" as used within the scope of the present application means that the selected electrode or the electrolyte layer located above the selected electrode is covered by the gas-permeable cover layer in the area stated in each case such that no contact between the selected electrode or the electrolyte layer located above the selected electrode and the aqueous measuring medium takes place.

In accordance with an embodiment of the present invention, the gas-permeable cover layer covers the working electrode in a range of at least 100 µm, more typically in a range of at least 500 µm, beyond the dimensions of the working electrode. If the gas-permeable cover layer only partially covers the counter electrode then it is typical that at least 90% of the counter electrode based on its surface is covered by the gas-permeable cover layer. In another typical variant of the invention the gas-permeable cover layer completely covers the working electrode as well as the counter electrode and can thus more effectively screen the electrodes from interferences from the measuring medium because the latter cannot diffuse to the electrodes on a direct path, i.e., without involvement of the electrolyte layer.

The gas-permeable cover layer can consist of any material which appears suitable to a person skilled in the art for the purposes described above. The gas-permeable cover layer typically comprises at least one polymeric material where polysiloxanes, polysulfones and/or polytetrafluoroethylene are typical. In particular, silicone rubbers can be used as polysiloxanes such as, for example, those that are commercially available under the trade name DELO-GUM® (DELO Company, Germany). Suitable polysulfones comprise in particular polysulfones with longer alkyl chains such as, for example, $C_{16}$ alkyl chains. Such a product is known under the trade name BIOBLAND® (ANATRACE Company, USA).

The gas-permeable cover layer can be produced in different ways. A typical method is to use prefabricated cover layers which are applied to the electrochemical sensor. In this case the membrane can be attached to the sensor by means of any techniques where gluing or laser welding are regarded as typical.

Alternatively, the gas-permeable cover membrane can be produced in situ by applying a solution of a suitable gas-permeable polymer or prepolymer to the electrochemical sensor and subsequently drying it. The polymer can be applied to the electrochemical sensor typically by spraying, dip coating, dispersing or screen printing a typically diluted solution of the polymer or prepolymer but is not limited to these methods. In this connection an organic solvent and in particular an organic solvent having a boiling point of ≤100° C. is typically used as a solvent, where the solvent can be varied depending on the properties of the polymer or prepolymer and/or the application technique, and can be selected accordingly by a person skilled in the art.

The gas-permeable cover layers obtained in this manner and used in an electrochemical sensor according to an embodiment of the invention usually have a thickness of about 5 µm to about 30 µm. In a typical variant the gas-permeable cover layer has a thickness of at least 30%, in particular a thickness of 50% to 100% of the thickness of the electrolyte layer used according to the invention.

The electrochemical sensor according to the invention is typically designed for multiple analyte determinations, i.e., analyte determinations that take place successively. This is especially desired in applications in which it is intended to measure a large number of samples with one sensor. Consequently, in a typical embodiment, the invention provides that the electrochemical sensor is designed as a sensitive component of a (flow through) measuring cell into which a sample liquid containing the analyte is introduced and which is, for example, a replaceable part of an analyzer.

The electrochemical sensor according to the invention is used to determine oxygen in an aqueous measuring medium which can be derived from any source. The term "determination of oxygen dissolved in an aqueous measuring medium" as used within the scope of the present application encompasses the determination of the presence or the concentration of dissolved oxygen in the aqueous measuring medium as well as the determination of the gas partial pressure of oxygen in the aqueous measuring medium. In a typical embodiment the aqueous measuring medium is a body fluid where whole blood is more typical.

In accordance with another embodiment, the present invention concerns a process for producing an electrochemical sensor according to various embodiments described herein, the process comprising the steps:

(a) providing at least one particulate material,
(b) mixing the particulate material with at least one binding agent and optionally further substances,
(c) processing the mixture obtained in step (b) to form a paste, (d) applying the paste obtained in step (c) to a carrier comprising a working electrode and a counter electrode and hardening the paste applied to the carrier, (e) applying a gas-permeable cover layer comprising at least one opening to the carrier obtained in step (d), and (f) optionally introducing a layer of a hydrophilic polymeric filling material into the opening of the gas-permeable cover layer applied in step (e) to the carrier.

For the purposes of producing the electrochemical sensors according to the invention an inorganic or organic particulate material containing at least one inorganic or organic binding agent which are each defined as above, and optionally further substances are mixed and processed to form a paste for the production of at least the paste according to step (c). After the paste has been applied to a carrier comprising a working electrode and a counter electrode, for example by screen printing or by means of knife coating techniques, and subsequently hardening the paste, a porous, non-swellable framework structure is formed which can be used as an electrolyte layer in an electrochemical sensor according to the invention.

After a gas-permeable cover layer comprising an opening has been applied to the carrier described above, which for example can be carried out by means of screen printing, while at the same time covering a predefined area of the carrier, and optionally additionally applying a layer of a hydrophilic polymeric filling material which is typically applied in the area of the opening of the gas-permeable cover layer to the carrier or to the electrolyte layer located thereon, it is possible to obtain an electrochemical sensor as disclosed in the present application. The production process described above provides that the paste as well as the electrodes can be applied to the carrier by means of screen printing and thus in a thin and defined layer thickness.

The process according to the invention typically additionally comprises the introduction of a liquid containing non-volatile electrolyte components, e.g., a liquid electrolyte into the porous, non-swellable framework structure and subsequently evaporating its volatile components. The liquid electrolyte which ensures the electrically conductive connection between the working electrode and the counter electrode in the sensor according to the invention can be formed from these non-volatile components. In this connection the liquid can be introduced into the pores of the non-swellable framework structure using techniques such as those described in connection with the elucidation of the electrochemical sensor.

Alternatively the non-volatile electrolyte components can be already introduced into a mixture which contains at least a particulate material with at least one binding agent and optionally further substances before formation of the porous, non-swellable framework structure which enables the solid components of the electrolyte to be uniformly distributed in a simple manner in the porous, non-swellable framework structure that is obtained after hardening the mixture.

In yet another typical embodiment of the invention, the process comprises introducing the liquid into a paste where the liquid can be added to the paste in particular before applying the same to a suitable carrier. In this embodiment a liquid is added which contains the non-volatile electrolyte components typically in a solvent that is miscible with the binding agent. This solvent can for example be a glycol such as ethylene glycol, propylene glycol or a mixture thereof which can optionally contain up to 20% (v/v) water.

In still another embodiment of the present invention, a method for determining oxygen dissolved in an aqueous measuring medium is provided comprising the steps:

(a) bringing the aqueous measuring medium into contact with an electrochemical sensor according to the invention, and (b) determining the oxygen dissolved in the aqueous measuring medium by measuring a signal generated by the electrochemical sensor.

In order to determine oxygen as a gaseous analyte, the electrochemical sensor according to the invention can be configured in any manner that enables a contact to be made between the electrochemical sensor and the aqueous measuring medium. Thus, the sensor can for example be configured as a sensitive component of a measuring cell into which the aqueous measuring medium containing the oxygen is introduced. Furthermore, the sensor together with further sensors which for example are used to determine different point-of-care parameters can be configured in replaceable measuring chambers (e.g., sensor cassettes).

A measurable signal is generated by the sensor depending on the presence and/or the amount of the analyte. The electrochemical sensor according to the invention is typically designed as an amperometric sensor in which the electrical current is evaluated or read out as the measuring signal using suitable means.

Figure 1A:
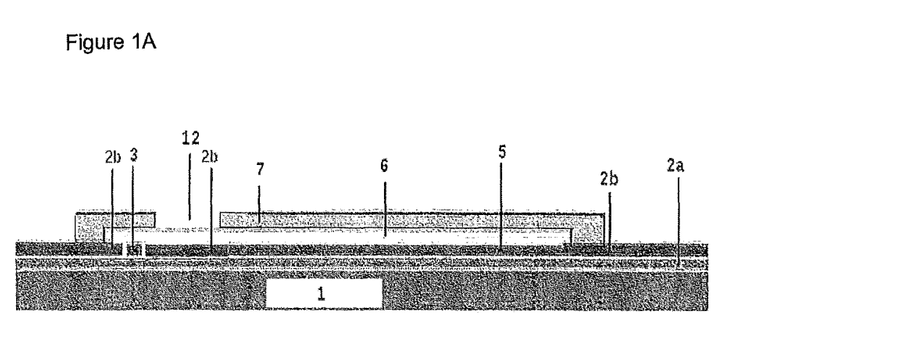
FIG. 1A shows a section through the channel area in an electrochemical $pO_2$ sensor according to an embodiment of the present invention.

FIG. 1A shows a section through the channel area in an electrochemical $pO_2$ sensor according to an embodiment of the present invention. A small metal plate coated with a layer of an electrical insulating varnish (2a) is used as a carrier (1) where said insulating varnish insulates the electrodes mounted thereon from the metal plate. A further insulating layer (2b) is applied to some areas (see FIG. 1B) of this continuous insulating layer (2a) and is provided in order to avoid interfering potentials or currents upon liquid contact.

A window is cut out in the measuring area in which the working electrode (3), the counter electrode (5) as well as the porous electrolyte layer (6) located above them, are arranged. The porous electrolyte layer (6) extends along the measuring channel and completely covers the active surfaces of the working electrode (3) as well as of the counter electrode (5). The gas-permeable cover layer (7) is arranged above the porous electrolyte layer (6) and has an opening (12) in the form of a gap between the working electrode (3) and the counter electrode (5) which separates the gas-permeable cover layer (7) into a partial area on the cathode side and a partial area on the anode side.

In the embodiment shown in FIG. 1A, the gas-permeable cover layer (7) completely covers the working electrode (3) as well as the counter electrode (5). In this case the working electrode (3) is covered by the gas-permeable cover layer (7) in a range of about 200 μm to about 600 μm, the width of the opening (12) in the gas-permeable cover layer (7) is usually in the range of about 100 μm to about 400 μm.

Figure 1B:
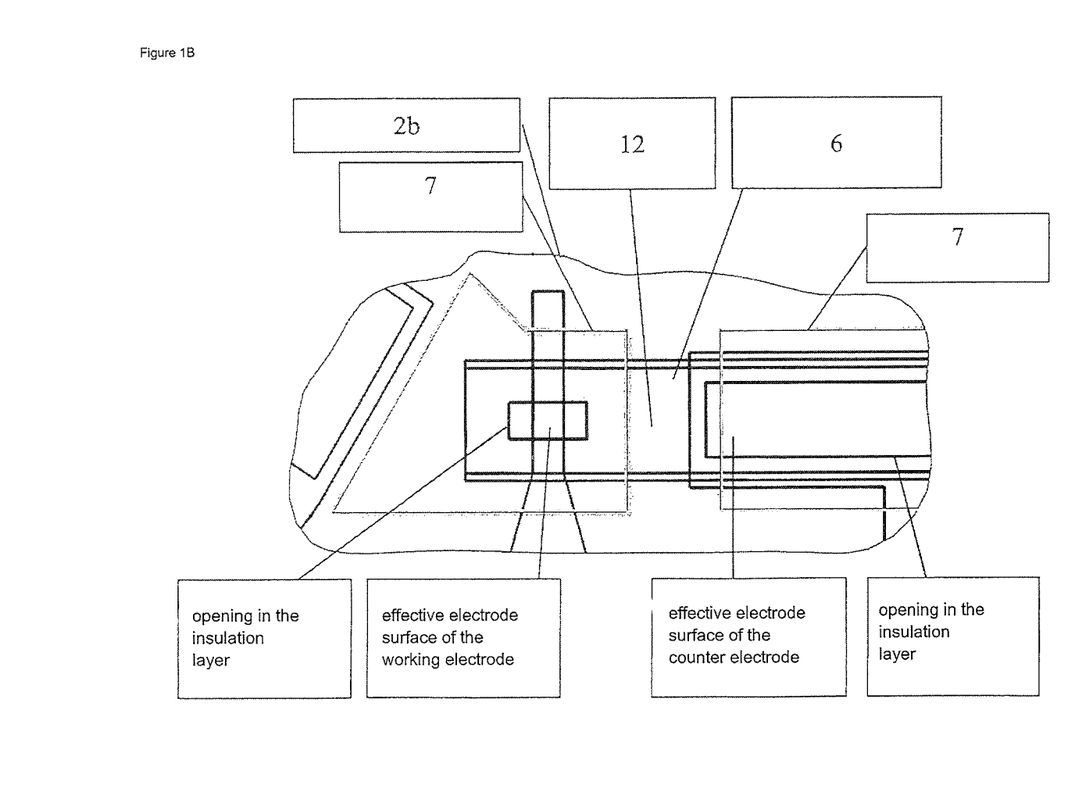
FIG. 1B shows a top view of the channel area of an electrochemical $pO_2$ sensor according to an embodiment of the present invention.

FIG. 1B shows a top view of the channel area of an electrochemical $pO_2$ sensor according to an embodiment of the present invention. In this embodiment in which a gap (12) is formed between the two partial areas of the gas-permeable cover layer (7), the surface of the working electrode (3) is completely covered by the gas-permeable cover layer (7) and the surface of the counter electrode (5) is only partially covered by the gas-permeable cover layer (7). The other reference numerals have the same meaning as stated for FIG. 1A.

In order that the invention may be more readily understood, reference is made to the following examples, which are intended to illustrate the invention, but not limit the scope thereof.

EXAMPLE 1

Production of a Screen-Printable Paste 12.0 g ethyl cellulose powder N50 and 192.0 g terpineol were weighed into a sealable jar and the mixture was stirred for 2 weeks at room temperature until the ethyl cellulose had completely dissolved. In order to prepare a quantity of 100 g of ready-to-use, screen-printable paste, subsequently 25.6 g of the ethyl cellulose solution that was obtained, 32.3 g phenol resin PR 373, 1.0 g of the antifoaming agent Byk 051 (Byk Chemie Company), 5.0 g benzyl alcohol and 2.9 g butyl diglycol were weighed into a beaker and this mixture was intensively stirred. 43.2 g of the zeolite LZ-Y 52 (Sigma-Aldrich Company, product No. 334448) was added to this mixture and the preparation was intensively stirred until the filler had homogeneously dispersed to obtain a screen-printable paste.

EXAMPLE 2

Determination of the Relative Liquid Uptake of a Paste Prepared According to Example 1 and Hardened In order to determine the relative liquid uptake of a paste produced according to Example 1, several microscope slides (76×26 mm, ISO Norm 8038/1, Roth Company) were weighed on an analytical balance ($m_{carrier}$). Test layers were subsequently applied to the microscope slides by applying the paste produced according to Example 1 to the microscope slides using an 80 μm spiral doctor knife The applied paste covered a rectangular area of approximately 60×18 mm. Because this area is variable, it was not determined exactly until the paste had hardened. 10-15 minutes after applying the paste, the test bodies were hardened in a drying cabinet for 4 h at 110° C. Subsequently the test bodies were stored in a desiccator (over CaO) until the measurement. The microscope slides with the hardened paste were again weighed ($m_{dry}$) and immediately afterwards immersed in each case in about 40 ml liquid which was in screw top plastic tins having a volume of 100 ml. During the measuring process the tins containing the immersed test bodies remained sealed.

The test bodies were removed from the tins at defined times, blotted and weighed in order to determine the amount of liquid taken up. The measurements were discontinued when the amount of liquid taken up and thus the mass ($m_{wet}$) remained constant. The measurements were carried out at room temperature and normal pressure. The relative liquid uptake was calculated for each test body from the measurements obtained as a mean of the corresponding measurements of at least three test bodies with a maximum standard deviation of 1%.

The respective relative liquid uptake was related to the dry weight of the hardened paste that had previously been determined (in each case minus the weight of the microscope slide): (relative liquid uptake [%]=[($m_{wet}$−$m_{carrier}$)/($m_{dry}$−$m_{carrier}$)−1]*100. The values for the relative liquid uptake change depending on the porosity of the hardened paste. Hardened pastes with an undesired high porosity have relative liquid uptakes between 50% and 70%, hardened pastes with an undesired low porosity have relative liquid uptakes of less than 20%. Hardened pastes which are used within the scope of the present invention have a porosity which results in a relative liquid uptake between 20% by weight and 50% by weight, typically between 26% by weight and 44% by weight.

EXAMPLE 3

Preparation of a Semi-Finished Sensor Having a Porous Electrolyte Layer

In order to produce a semi-finished sensor which can be used as a component of an electrochemical sensor according to the present invention, the paste produced according to Example 1 was applied to a screen, applied by means of screen printing to a suitable carrier comprising a working electrode and a counter electrode and hardened at an elevated temperature. The thickness of the hardened layer was 10-20 μm.

EXAMPLE 4

Preparation of a Suitable Semi-Finished Sensor for $O_2$ Sensors having a Porous Electrolyte Layer In order to produce a semi-finished sensor which can be used as a component of an electrochemical $O_2$ sensor according to the present invention, 0.310 g NaCl (p.a.) and 0.066 g polyethylene glycol 6000 (for synthesis) were dissolved in 1.6 g deionized water. A solution of 0.900 g glycerol (p.a.) in 23.15 g ethylene glycol was subsequently added to the solution obtained in this manner and stirred until a clear solution was obtained.

In order to produce the semi-finished sensor, 4.2 g of the aqueous ethylene glycol solution was stirred into 100 g of the paste produced according to Example 1 after which the paste containing the liquid electrolytes was applied by means of screen printing to a suitable carrier and hardened at an elevated temperature.

EXAMPLE 5

Applying a Partially Open, Gas-Permeable Cover Layer to the Semi-Finished Sensor Prepared According to Example 4

A gas-permeable cover layer which in turn has an opening was applied by means of screen printing to the semi-finished sensor according to Example 4. For this purpose an 80% solution of DELO-GUM® SI 480 (DELO Company) in n-heptane was applied to the semi-finished sensor by means of screen printing and hardened at an elevated temperature.

The screen printing structure was selected such that a slit-shaped opening having an average width of 300±100 μm was produced, where the cathode edge on the anode side was covered by 400±100 μm by the partial area on the cathode side of the gas-permeable cover layer and the anode edge on the cathode side made a flush seal with the partial area on the anode side of the gas-permeable cover layer.

EXAMPLE 6

Application of a Layer of a Hydrophilic Polymeric Filling Material to the Semi-Finished Sensor Prepared According to Example 5

An optional layer of a hydrophilic polymeric filling material was applied to the semi-finished sensor prepared according to Example 5 for example by being dispensed thereon. For this purpose for example a 1% solution of a hydrophilic polyether-polyurethane copolymer having an at least 50% water uptake was introduced into the opening between the partial area on the cathode side and on the anode side of the gas-permeable cover layer by means of a microdispensing device in the form of a drop of about 10 nl in size and subsequently dried.

Because the absorption used for cutting out the template is noisy, the template per se also has a corresponding noise component, which has an influence which is not negligible on the result of the CCF upon the cross-correlation with the target signal. The noise of the quadratic function (parabola), however, is zero, whereby the noise component of $R_{xy}$ is also minimized.

It is noted that terms like "preferably", "commonly", and "typically" are not utilized herein to limit the scope of the claimed invention or to imply that certain features are critical, essential or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined by the appended claims. More specifically, although some aspects of the present invention are identified herein as preferred or particularly advantageous, it is contemplated that the preset invention is not necessarily limited to these preferred aspects of the invention.

What is claimed is:

1. An electrochemical sensor for the determination of oxygen dissolved in an aqueous measuring medium, comprising:
   a working electrode and a counter electrode,
   an electrolyte layer arranged between the working electrode and the counter electrode, wherein the electrolyte layer comprises at least one particulate material and at least one binding agent which together form a porous, non-swellable framework structure, and wherein the pores of the non-swellable framework structure are intended to take up a liquid electrolyte or said pores contain said liquid electrolyte, and
   a gas-permeable cover layer arranged over the electrolyte layer, wherein the gas-permeable cover layer comprises at least one opening which enables a contact of a partial area of the electrolyte layer with the aqueous measuring medium, and wherein the opening is arranged at least partially over the area of the electrolyte layer that lies between the working electrode and the counter electrode.

2. The electrochemical sensor according to claim 1, wherein the opening has a width in the range of about 50 μm to about 500 μm.

3. The electrochemical sensor according to claim 1, wherein the opening has a width in the range of about 100 μm to about 300 μm.

4. The electrochemical sensor according to claim 1, wherein the opening has a slit-shaped or window-like design.

5. The electrochemical sensor according to claim 1, wherein the opening is filled with a hydrophilic polymeric filling material, and wherein the hydrophilic polymeric filling material differs from the material that forms the gas-permeable cover layer.

6. The electrochemical sensor according to claim 5, wherein the hydrophilic polymeric filling material is a polyether-polyurethane copolymer or a polyvinyl pyrrolidone.

7. The electrochemical sensor according to claim 1, wherein the gas-permeable cover layer completely covers the working electrode and at least partially covers the counter electrode.

8. The electrochemical sensor according to claim 1, wherein the gas-permeable cover layer covers at least 90% of the counter electrode based on its surface area.

9. The electrochemical sensor according to claim 1, wherein the gas-permeable cover layer comprises a polymeric material selected from the group consisting of a polysiloxane, a polysulfone and a polytetrafluoroethylene.

10. The electrochemical sensor according to claim 1, wherein the sensor is an amperometric sensor.

11. A method for the determination of oxygen dissolved in an aqueous measuring medium comprising:
    bringing the aqueous measuring medium into contact with an electrochemical sensor according to claim 1, and
    determining the oxygen dissolved in the aqueous measuring medium by measuring a signal generated by the electrochemical sensor.

* * * * *